United States Patent [19]

Goldman et al.

[11] 4,095,588
[45] Jun. 20, 1978

[54] VASCULAR CLEANSING

[76] Inventors: Joseph Goldman, 8 MacIntosh La., Monsey, N.Y. 10252; Guy Adams, 5 Briarwood Ave., Monroe, N.Y. 10950; Shirley Goldman, 8 MacIntosh La., Monsey, N.Y. 10252

[21] Appl. No.: 706,905

[22] Filed: Jul. 19, 1976

[51] Int. Cl.$^2$ ............................................. A61B 17/00
[52] U.S. Cl. .................................................. 128/1.5
[58] Field of Search ................. 128/1.5, 1.3; 361/153, 361/154

[56] References Cited

U.S. PATENT DOCUMENTS

| 1,418,903 | 6/1922 | Benson | 128/1.5 |
| 3,864,608 | 2/1975 | Normile et al. | 361/154 |
| 3,915,151 | 10/1975 | Kraus | 128/1.5 |
| 4,008,420 | 2/1977 | Navratil | 361/153 |

FOREIGN PATENT DOCUMENTS

| 305,664 | 2/1933 | Italy | 128/1.3 |

*Primary Examiner*—Robert W. Michell
*Assistant Examiner*—Michael H. Thaler
*Attorney, Agent, or Firm*—Richard G. Geib

[57] ABSTRACT

Encircling with a magnetic field controllable by a variable frequency and amplitude to propel red blood cells radially while rotating about a vascular axis so as to loosen and clear away vascular accumulations tending to block the vascular system.

8 Claims, 5 Drawing Figures

VASCULAR CLEANSING

BACKGROUND

It has been stated, as for example in prior art U.S. Pat. No. 3,337,776, a variable or continuous magnetic field can have beneficial biomedical applications. Other examples than the therapeutical purposes of this patent were also noted in the prior art. More particularly, in the promoting of the healing of bone fractures there are prior art U.S. Pats. 3,890,953 and 3,915,151. Also noted was U.S. Pat. No. 3,358,676 which is suggestive of means for producing a varying magnetic field that will act on an element introduced to a vascular system to impart thereto a vibrational or rotational motion such that propulsion is effected by contact with the vascular system.

FIELD OF INVENTION

In contrast to the above this invention, while also relating generally speaking to biomedical applications of a controllable magnetic field, is concerned with oscillating and rotating by a magnetic field the red corpuscles in a vascular system whereupon the red corpuscles due to their rotational oscillations will cleanse the vascular system.

SUMMARY

It is a more particular object of this invention to utilize clock control of a digital integrated circuit to pulse deflection amplifier means in varying a magnetic field frequency and amplitude in rotating the field.

A further explanation of the aforesaid object in terms of the specific utility found therefor would be to create the aforesaid magnetic field to effect motion of the red corpuscles in the blood stream of a vascular system due to the iron oxide content thereof whereby these red cells may cleanse the vascular system by scrubbing the walls thereof.

DRAWINGS

DETAILED DESCRIPTION

Figure 1:
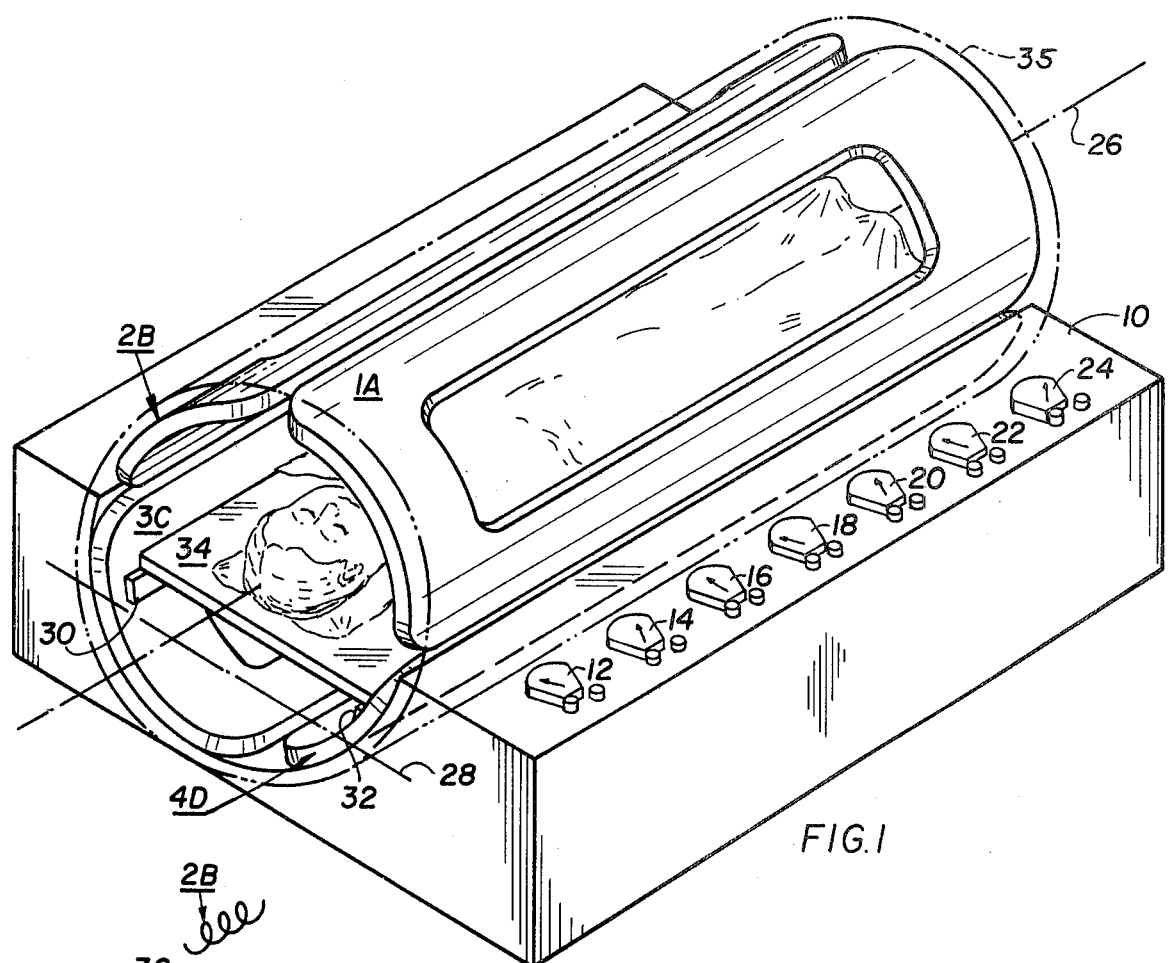
FIG. 1 is an isometric view of a laboratory station as may be used for cleansing human vacular system in accordance with this invention.

With more particular reference to FIG. 1 there is shown thereby a lab table 10 specially adapted to monitor life signs of a human, such as blood pressure, body temperature, pulse rate, eye movement, body moisture and alpha wave frequency and illustrate same by way of meters, if desired, 12, 14, 16, 18, 20, 22 and 24 with appropriate switches and or warning indicators (lights, etc.) as will be readily appreciated by those skilled in the art.

The table 10 is specially adapted to mount coils 1A, 2B, 3C and 4D about a longitudinal axes 26 and a lateral axis 28. Within these coils below the aforesaid axis is mounted, as by rails 30 and 32, a table 34 on which a human, as shown, may comfortably lay. Table 34 is offset from center and adjustable so that the person laying thereon is in the center of the coils on axis 26. Shown by dash lines 35 for drawing clarity another coil may be adpated about the coils 1A, 2B, 3C and 4D. This coil would, if required, be activated to nagate the earth's magnetic field such that aside from the field activated by coils 1A, 2B, 3C and 4D the person on table 34 is in a magnetic "free area" for lack of better descriptive terminology. As will be readily appreciated again by one versed in the technology the earth's magnetic field exerts a coercive force of 0.9 OER as measured in Philadelphia, P., U.S.A. Rather than using a coil 35 to create a separate negating field one may orient bench 10 so that the longitudinal axis 26 is oriented on the earth's East-West axis. With such orientation the human will be perpendicular to the magnetic lines of the earth and the earth's magnetic field will be negated.

Figure 2:
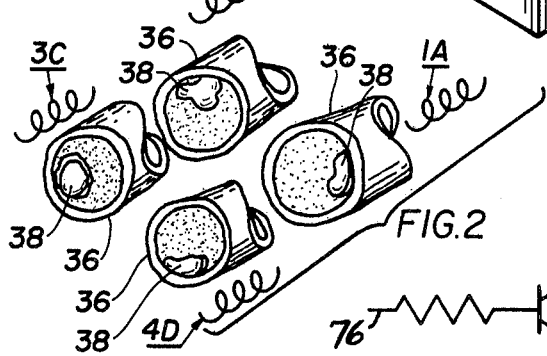
FIG. 2 is a composite of an artery or vein of a vascular system showing varied propulsion of a blood cell therein so as to scrub the walls thereof all in accordance with the principles of this invention.

In any event as the red blood cells comprise iron oxide they are magnetically attractable. With reference to FIG. 2 it is seen how in an artery 36, for example, such a red corpuscle 38 may be moved outwardly by rotating the magnetic field due to varying frequency and amplitude of the electricity to coils 1A-3C, 2B-4D, etc.

The principal object of the invention may be thus realized by the rotary bombardment of the walls of vascular element 36 due to this rotating field. The debris so removed in opening the vascular system is flushed by the flow of the blood to the body organs for disposal. In other words with this invention a human with restricted arteries can be moved into the influence of the fields of coils 1A, 2B, 3C and 4D or any combination of these coils which fields may be rotated by means explained below with varying frequency and amplitude so as to revolve about axis 26 thereby oscillating blood cells 38 so that, by such oscillation which is to be visualized in the mind as it is not readily illustratable, the vascular elements, illustrated as artery 36, may be scrubbed by the red cells to loosen accumulations tending to restrict flow in the vascular system.

Figure 3:
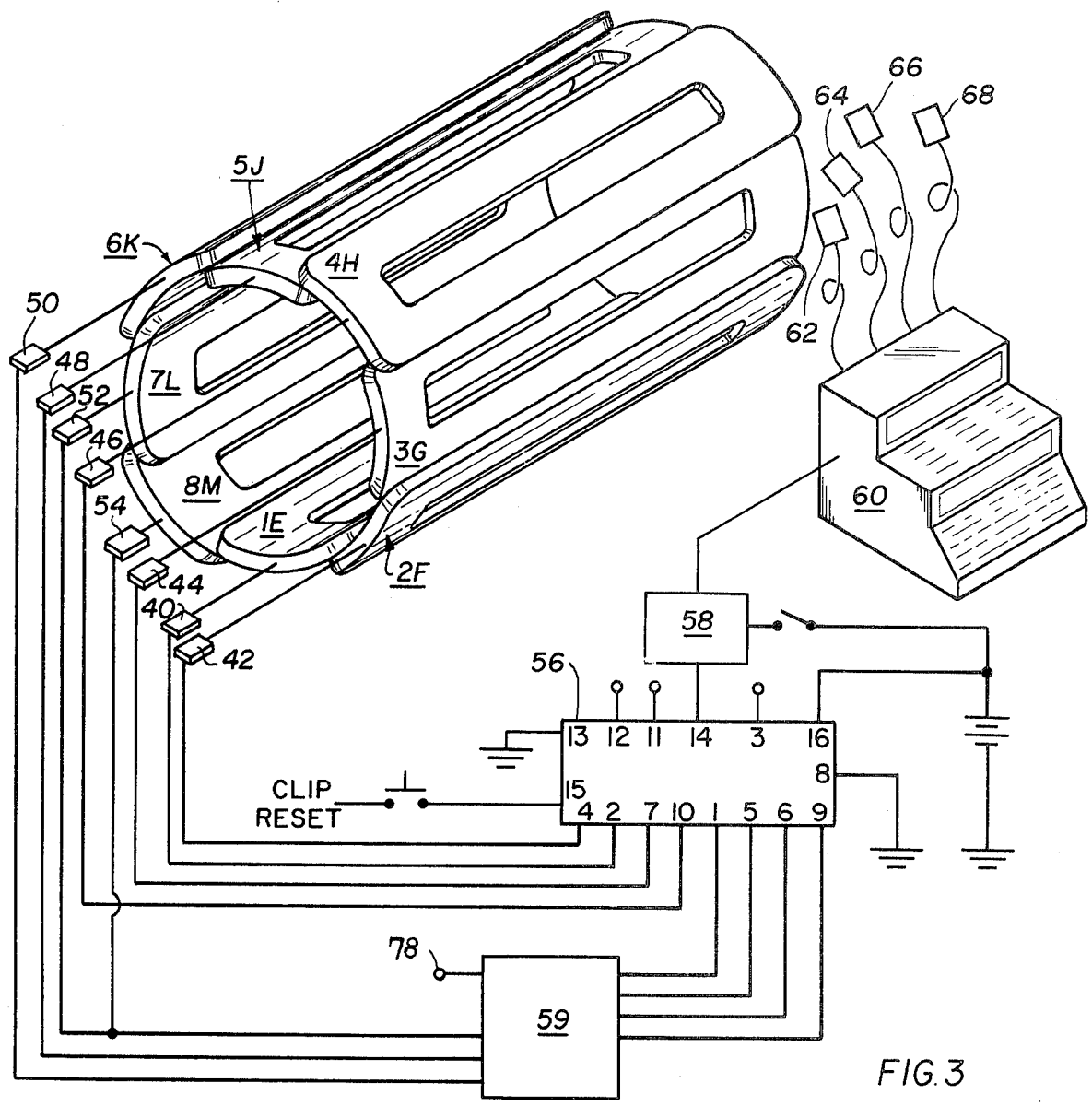
FIG. 3 is an isometric showing of a preferred alternate of a device to creae a rotatable magnetic field with associated circuitry in block form.

With reference now to FIG. 3 there is shown a preferred coil means having eight coils 1E, 2F, 3G, 4H, 5J, 6K, 7L, and 8M whose edges slightly overlap. These coils have deflection amplifier means 40, 42, 44, 46, 48, 50, 52 and 54 of a circuit as may be understood from a description of FIG. 4 hereinafter.

Figure 5:
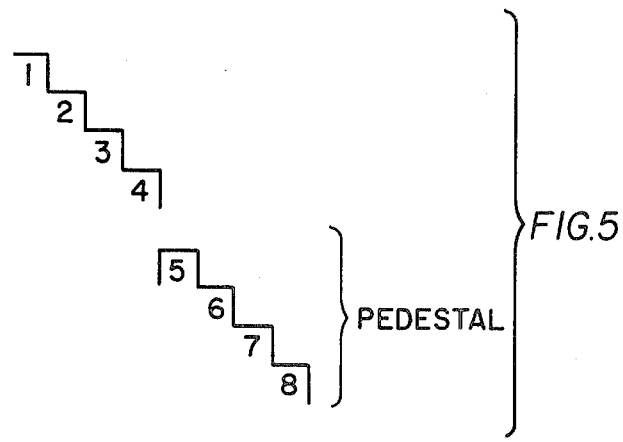
FIG. 5 is an illustration of the sequential operation of the fields of the coils in FIG. 3.

A plurality of leads connect the deflection amplifiers 40, 42, 44 and 46 to a digital integrated circuit 56, such a circuit being commonly sold under the 4017 part designation, as by RCA, etc. In essence this circuit with its pin connections used as indicated permits the timing sequence for the coils 1E, 2F, 3G and 4H as illustrated by FIG. 5. Deflection amplifiers 48, 50, 52 and 54 are connected also via a plurality of leads to a DC pedestal 59 and thence to clocked chip 56 via another plurality of leads. Thus the coils 5J 6K, 7L and 8M can experience the timing sequence shown by FIG. 5.

In order to clock chip 56 a variable oscillator 58, as will be as readily familiar to one versed in the art as the DC pedestal is, is connected between chip 56 and computer 60 programmed to with sensor pads, 62, 64, 66 and 68 being examples, provide feedback that permits control of the fields in accordance with a persons ability to take treatment.

Figure 4:
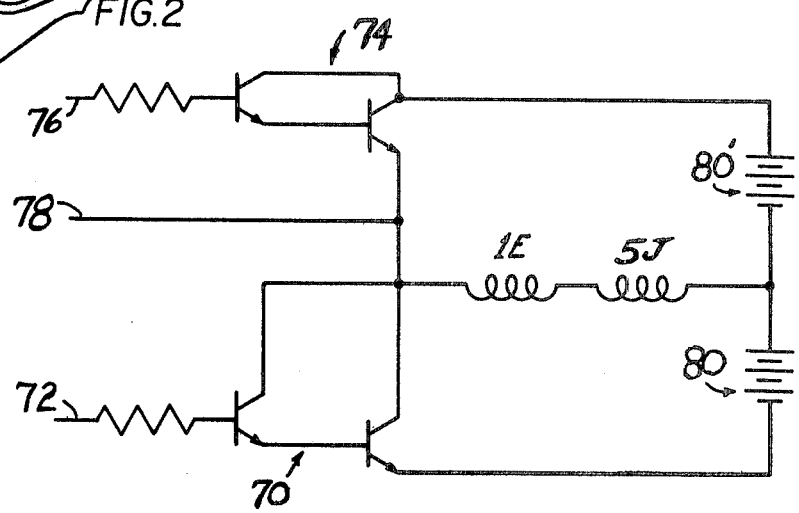
FIG. 4 is a circuit diagram of a deflection amplifier in accordance with the principles of this invention.

With reference now to FIG. 4 the deflection amplifier is shown in combined form therein to have one darlington circuit 70 with its input control terminal 72 for connection to chip 56. Another darlington circuit 74 with terminal 76 is also employed with darlington circuit 72. In order to create current by either a common lead 78 that is connected to common lead 78 of pedestal 59 see FIG. 3. This combined amplifier is shown to provide for field reversal in coils 1E and 5J connected together between darlington 72 and source 80 or between darlington 74 and source 80' in dependence upon the bias at terminal 72 or 76.

OPERATION

In operation a switch (See FIG. 3) is closed so as to energize variable oscillator 58 to start count in binary 56. This will provide sequential signals to terminal 72 thence 76, for example such that an electromagnetic field of one polar type is created from source 80 through darlington 70 and coils 5J and 1E, and of another polar type from source 80' through darlington 74 in coils 1E and 5J. As will be appreciated the binary 56 is such as to walk this around the axis 26 allowing gradual decay and buildup of adjacent influencing fields. Therefore the field amplitude will vary as the control signals to darlington devices rises and falls. This will of course be at a frequency determined by variable oscillator 58 as will be readily apparent to one skilled in the art.

Monitoring of life signs by computer 60 allows automatic control of the oscillator to control frequency at that level which is acceptable to the system being treated and if necessary terminate the treatment.

Having described an operative form of our invention it is now desired to set forth the protection sought by these Letters Patent by the appended claims.

We claim:

1. A method of cleansing a vascular system comprising the steps of arranging a plurality of electromagentic coils to be separate from each other about an axis in the form of an annular electromagnetic means said coils being elongated in a direction perpendicular to the magnetic axis of the coils;
   connecting coils in series on diametrically opposite sides of the axis;
   providing an oscillating signal to an integrated circuit;
   producing sequential control signals within the integrated circuit and thereby providing control signals to a plurality of current controlling amplifier means;
   valving current at a variable frequency and amplitude from the amplifier means in a first direction from one coil via the connection to another coil diametrically opposed and thence in a second direction from said another to said one of said electromagnetic coils in accordance with the sequence of the control signals and with a rising and falling amplitude effected by the state of conduction of the amplifier means and thereafter walking said current around to pass from one to the other of another set of connected diametrically opposed coils to create a rotation of a variable frequency and amplitude electromagnetic field created by and about the diametrically opposed coils and around the axis of the annular electromagnetic means; and
   oscillating and rotating red corpuscles in the vascular system by the variable frequency and amplitude electromagnetic field rotating from one coil and another coil to adjacent diametrically opposed coils about said axis of the annular electromagnetic means so as to scrub the vascular system by contact of the red corpuscles with the walls thereof and the normal flow in the system.

2. A method of cleansing a vascular system of a person said method including the following steps:
   resting the person on a table;
   placing the table in an environment where the effects of the earth's magnetic field are minimized;
   orienting a plurality of separate coils to have two connected in series on diametrically opposite sides of and about the table to have a coil on top and a coil on bottom as one pair and a coil on the left and a coil on the right as another pair thereby encircling an axis passing through the person in the environment aforesaid; and
   conducting current of a variable frequency and amplitude through one pair and thence the another pair in one direction and thereafter conducting current in another direction in the one pair and thence the another pair to create an electromagnetic field about one pair and then the another pair of coils, at least, so as to oscillate and rotate red corpuslces in the vascular system to contact and thereby scrub the walls of the system with debris loosened being carried away by flow of the system.

3. A means to propel a red corpuscle in a vibratory and rotary fashion, said means comprising an electronic circuit and magnetic means including:
   a source of electrical energy;
   a variable oscillator connected to said source;
   a binary counter means connected to said oscillator to produce sequential outputs;
   a plurality of deflection amplifier means connected to be operable by the outputs of said binary counter means in a sequential manner, said amplifier means thereby controlling electrical energy from said source;
   a plurality of separate coils connected in separate pairs about an axis in series between said deflection amplifier means and said source so as to besequentially operated in creating an electromagnetic field from one coil to the other and back again and thence to adjacent separate coils for rotation of the electromagnetic field from one pair of coils to another; and
   a table within the space encircled by said plurality of coils, said table being located so as to place a person along the axis such that the red corpuscles of the person's vascular system are within the electromagnetic field between the coils creating same.

4. The means of claim 3 where said deflection amplifier means are each comprised of a pair of darlington transistors arranged to have the emitter of one of the pair and the collector of another of the pair connected via one of said separate pairings of said coils to a power source with a common lead between to a DC pedestal so as to permit field reversal of said one of said separate pairings of said coils when one of the pair is biased on and another of the pair is not being biased to its conducting state.

5. A means according to claim 3 and further including means to monitor life signs of a person, said means operatively connected to the variable oscillator.

6. A means according to claim 3 wherein a human body is oriented on the axis of the plurality of coils so as to be in the center of a magnetic field controlled by said plurality of deflection amplifier means.

7. A means according to claim 3 wherein the separate coils are inclusive of at least four individual coils coupled electronically by said binary counter means so as to walk the magnetic field about the axis of the plurality of coils.

8. A means according to claim 3 wherein the coils are inclusive of at least eight coils equally disposed about an axis electronically connected by said binary counter means to couple two at a time to walk the field about the axis.

* * * * *